US010441704B2

(12) United States Patent
Crnkovich et al.

(10) Patent No.: US 10,441,704 B2
(45) Date of Patent: *Oct. 15, 2019

(54) AUTOMATIC DETECTION AND ADJUSTMENT OF A PRESSURE POD DIAPHRAGM

(71) Applicant: Fresenius Medical Care Holdings, Inc., Waltham, MA (US)

(72) Inventors: Martin Crnkovich, Walnut Creek, CA (US); Lee Tanenbaum, Walnut Creek, CA (US); Michael Emmanuel Kotsos, Walnut Creek, CA (US); Fei Wang, Concord, CA (US); Alex Brown, Danville, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 47 days.

This patent is subject to a terminal disclaimer.

(21) Appl. No.: 15/832,095

(22) Filed: Dec. 5, 2017

(65) Prior Publication Data
US 2018/0093033 A1 Apr. 5, 2018

Related U.S. Application Data

(63) Continuation of application No. 15/022,932, filed as application No. PCT/US2014/067200 on Nov. 25, (Continued)

(51) Int. Cl.
*G01L 7/08* (2006.01)
*A61M 1/36* (2006.01)
(Continued)

(52) U.S. Cl.
CPC ............ *A61M 1/3639* (2013.01); *A61M 1/16* (2013.01); *A61M 1/34* (2013.01); *A61M 1/3403* (2014.02);
(Continued)

(58) Field of Classification Search
None
See application file for complete search history.

(56) References Cited

U.S. PATENT DOCUMENTS 3,635,089 A  1/1972 Harding et al.
4,666,598 A  5/1987 Heath et al.
(Continued)

FOREIGN PATENT DOCUMENTS

CN  2302012 Y  12/1998
CN  1970099 A  5/2007
(Continued)

OTHER PUBLICATIONS

COBE Centrysystem 3 Dialysis Control Unit (Operator's Manual); Sep. 1988; COBE Laboratories, Inc.; Lakewood, CO (see p. 4-33 A-V Pressure Not Changing Alarm).
(Continued)

*Primary Examiner* — Andre J Allen
(74) *Attorney, Agent, or Firm* — Kilyk & Bowersox, P.L.L.C.

(57) ABSTRACT

A system for controlling the position of a diaphragm in a diaphragm-containing pressure pod, is provided. The system can include a peristaltic pump, a pressure pod having a flow-through fluid side and a gas side that are separated by a diaphragm, and a pressure sensor operatively connected to the gas side. The pressure sensor is configured to sense pulses of pressure resulting from movement of the diaphragm and caused by the action of the peristaltic pump. A gas source and a valve can be in fluid communication with the gas side of the pressure pod and can be configured to provide gas to, or vent gas from, the gas side. A controller receives pressure signals from the pressure sensor and
(Continued)

controls the valve in response, and in so doing, controls the position of the diaphragm. Methods for positioning the diaphragm are also included.

21 Claims, 5 Drawing Sheets

Related U.S. Application Data 2014, now Pat. No. 9,833,554, which is a continuation of application No. 14/139,081, filed on Dec. 23, 2013, now Pat. No. 9,545,423.

(51) Int. Cl.
    *A61M 1/16* (2006.01)
    *A61M 1/34* (2006.01)

(52) U.S. Cl.
    CPC ........ *A61M 1/3607* (2014.02); *A61M 1/3641* (2014.02); *G01L 7/088* (2013.01); *A61M 2205/3331* (2013.01); *A61M 2205/3344* (2013.01); *A61M 2205/3379* (2013.01); *A61M 2205/50* (2013.01)

(56) References Cited

U.S. PATENT DOCUMENTS

| | | | |
|---|---|---|---|
| 5,554,113 | A | 9/1996 | Novak et al. |
| 5,641,911 | A | 6/1997 | Ryhänen |
| 5,693,008 | A | 12/1997 | Brugger et al. |
| 5,720,598 | A | 2/1998 | de Chizzelle |
| 5,722,399 | A | 3/1998 | Chevallet et al. |
| 6,014,800 | A | 1/2000 | Lee |
| 6,016,705 | A | 1/2000 | Baur et al. |
| 6,526,357 | B1 | 2/2003 | Soussan et al. |
| 7,013,223 | B1 | 3/2006 | Zhang et al. |
| 7,487,681 | B1 | 2/2009 | Allen |
| 7,566,205 | B2 | 7/2009 | Kinugawa |
| 8,092,414 | B2 | 1/2012 | Schnell et al. |
| 8,197,231 | B2 | 6/2012 | Orr |
| 8,210,049 | B2 | 7/2012 | Brugger |
| 8,273,049 | B2 | 9/2012 | Demers et al. |
| 8,292,594 | B2 | 10/2012 | Tracey et al. |
| 8,323,194 | B2 | 12/2012 | Robinson |
| 8,357,298 | B2 | 1/2013 | Demers et al. |
| 8,429,979 | B2 | 4/2013 | Kuwahara et al. |
| 8,617,070 | B2 | 12/2013 | Imran |
| 8,960,010 | B1 | 2/2015 | Crnkovich et al. |
| 9,833,554 | B2 | 12/2017 | Crnkovich et al. |
| 2008/0216898 | A1 | 9/2008 | Grant et al. |
| 2009/0071258 | A1 | 3/2009 | Kouda et al. |
| 2013/0115105 | A1 | 5/2013 | Tracey et al. |
| 2014/0199193 | A1 | 7/2014 | Wilt et al. |
| 2014/0219829 | A1 | 8/2014 | Matsuo et al. |
| 2015/0306299 | A1 | 10/2015 | Stuva et al. |
| 2016/0228631 | A1 | 8/2016 | Crnkovich et al. |
| 2017/0143886 | A1 | 5/2017 | Wilt et al. |

FOREIGN PATENT DOCUMENTS

| | | |
|---|---|---|
| CN | 101011610 A | 8/2007 |
| CN | 101421602 A | 4/2009 |
| EP | 0 330 891 A1 | 9/1989 |
| WO | 2009/127683 A1 | 10/2009 |
| WO | 2013027621 A1 | 2/2013 |
| WO | 2015099932 A1 | 7/2015 |

OTHER PUBLICATIONS

Office Action for Chinese Patent Application No. 201480070388.0, issued by the Chinese State Intellectual Property Office (SIPO), dated Mar. 5, 2018, including search report and English-language translation, 14 pages.

International Search Report and Written Opinion issued in corresponding International Patent Application No. PCT/US2014/067200 dated Feb. 24, 2015 (11 pages).

Office Action for Japanese Patent Application No. 2016-541504, issued by the Japan Patent Office, dated Sep. 5, 2017, including English-language translation, 9 pages.

ies, however, additional hardware and software is implemented to utilize these module level controls as an automatic machine feature. In the case of the arterial pressure pod, the machine software monitors the arterial pressure. If the periodic arterial pressure pulses caused by the blood pump rotation are not detected, or if other predictable pressure signals or fluctuations caused by other factors are not detected, the software algorithm issues a command to activate the level control for the arterial pressure pod, at least momentarily, to push, pull, or otherwise force the diaphragm away from the shell wall. For the venous pressure pod, the machine software monitors the venous pressure. If the periodic venous pressure pulses caused by the blood pump rotation are not detected, or if other predictable pressure signals or fluctuations caused by other factors are not detected, the software algorithm issues a command to activate the level control for the venous pressure pod, at least momentarily, to push, pull, or otherwise force the diaphragm away from the shell wall. For either pressure pod, the system can automatically, at least momentarily, turn on a level down pump or open a level up valve and automatically adjust the diaphragm away from the shell wall. For either pressure pod, additional adjustments can also be provided to force the diaphragm away from the shell wall or to force the diaphragm further away from the shell wall. The algorithm can implement a pulse width modulated control signal to precisely meter an amount of pressurized gas to move the diaphragm, or precisely meter an amount of gas to be vented from the pressure pod.

The present teachings free a user from the task of manually positioning the diaphragm and provide more accurate and timely level adjustment than can be achieved by manual means.

AUTOMATIC DETECTION AND ADJUSTMENT OF A PRESSURE POD DIAPHRAGM

CROSS-REFERENCE TO RELATED APPLICATIONS

This application is a continuation of U.S. patent application Ser. No. 15/022,932, filed Mar. 18, 2016, now U.S. Pat. No. 9,833,554 B2, issued on Dec. 5, 2017, which in-turn is a 371 filing from International Application No. PCT/US2014/067200, filed Nov. 25, 2014, which is a continuation of U.S. patent application Ser. No. 14/139,061, filed Dec. 23, 2013, now U.S. Pat. No. 8,960,010 B1, issued on Feb. 24, 2015, all of which are incorporated herein by reference in their entities.

FIELD OF THE INVENTION

The present invention relates to a method and system for the automatic detection and adjustment of a pressure pod diaphragm used in an airless bloodline system.

BACKGROUND OF THE INVENTION

Airless bloodline systems have been implemented to include arterial and venous pressure monitor features known as "pressure pods." These pods consist of a molded plastic feature integrated into the bloodline system to transmit pressure information from a blood side of the pod, across a thin diaphragm, to a measurement feature of the machine. Under certain operating conditions, for example, caused by operator errors, leaks, or damaged tubing, there is a possibility that the diaphragm can become pressed against the rigid inner surface or shell wall of the pressure pod, as shown in FIG. 2B FIG. 2. When this happens, the pressure monitoring feature of the dialysis machine is no longer able to respond to pressure increases and records a constant incorrect pressure reading. When the pressure pod diaphragm gets pushed against the pressure pod inner surface, the orientation prevents increased pressure from being monitored. A user must visually detect this condition and manually adjust the diaphragm.

SUMMARY OF THE INVENTION

The present teachings relate to a system and method for detecting and automatically adjusting the position of a pressure pod diaphragm within an airless bloodline system. The method uses an algorithm to detect the position of the diaphragm and automatically uses pressure adjustments to move the diaphragm away from the shell wall. The system can include an arterial pressure pod located at an inlet of an arterial blood pump module, and a venous pressure pod located on the venous (outlet) side of a dialyzer. A pressure port can be connected to a level detector module of the hemodialysis system. The diaphragm, when properly positioned within the pressure pod, is adequately flexible to transmit blood pressure information across the entire pressure monitoring range.

An existing machine drip chamber level adjustment feature contained within an arterial blood pump and level detector module can be applied to manipulate the position of the pressure pod diaphragm. The conventional use of these level controls is for manual operator adjustment of the liquid/air level in the arterial and venous drip chambers of a conventional bloodline. In accordance with the present

BRIEF DESCRIPTION OF THE DRAWINGS

The invention may be more fully understood with reference to the accompanying drawings. The drawings are intended to illustrate, not limit, the present teachings.

DETAILED DESCRIPTION OF THE INVENTION

Figure 1A:
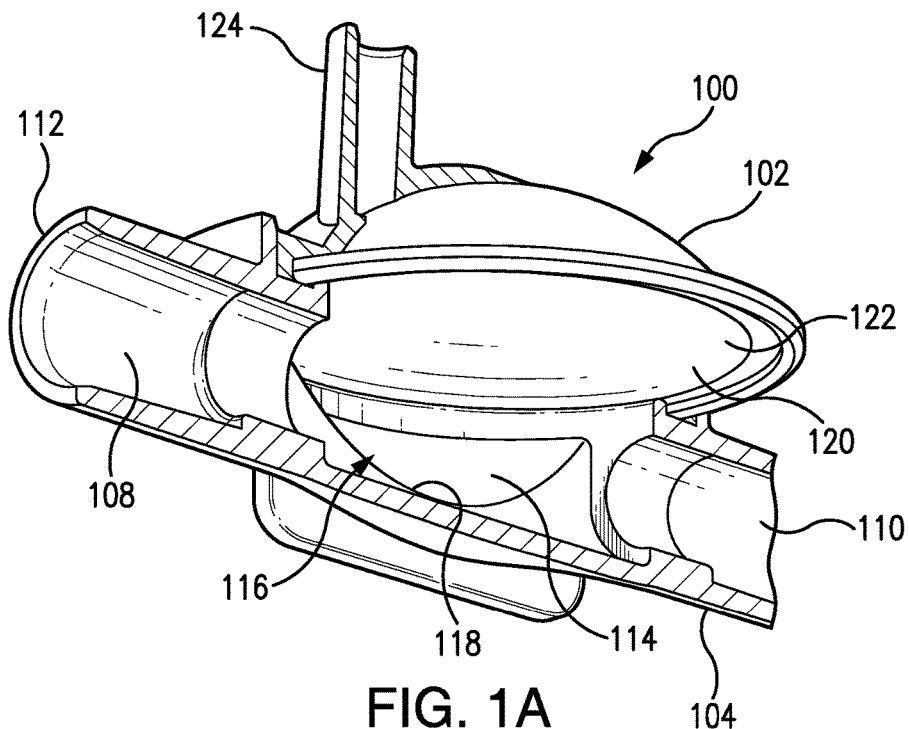
FIG. 1A is a perspective view in partial cross-section showing a flow-through pressure pod, with the diaphragm removed, that can be used in accordance with the present teachings.

According to one or more embodiments of the present invention, a system is provided for controlling the position of a diaphragm in a diaphragm-containing pressure pod. The system can comprise a fluid pump, a pressure pod, a pressure sensor operatively connected to the pressure pod, and a controller configured to receive a pressure signal generated by the pressure sensor and to control a gas pressure inside the pressure pod based on the pressure signal received. Controlling the gas pressure inside the pressure pod can be used to position the diaphragm within the pressure pod so that can it can accurately generate pressure measurements.

The pressure pod can comprise any of a variety of pressure pods used to measure the pressure of a fluid flowing through the pod. The pressure pod can comprise of an interior, defining a flow-through fluid side and a gas side. The flow-through fluid side and the gas side can be separated from one another by the diaphragm. Exemplary pressure pods that can be used in accordance with the present teachings include those shown and described, for example, in U.S. Pat. No. 8,210,049 B2, U.S. Pat. No. 8,092,414 B2, U.S. Pat. No. 6,526,357 B1, U.S. Pat. No. 3,863,504, and European Patent Application Publication No. 0 30 891 A1, each of which is incorporated herein in its entirety, by reference.

A fluid conduit can be provided in fluid communication with the flow-through fluid side of the pressure pod. The fluid conduit can be operatively positioned with respect the fluid pump such that the pump can move fluid through the conduit and force fluid through the flow-through fluid side of the pressure pod. In some cases, the fluid pump can be arranged to push fluid through the fluid conduit and through the pressure pod. In other embodiments, the fluid pump can be arranged to pull fluid through the conduit and through the pressure pod. The fluid pump can comprise a peristaltic pump and the fluid conduit can be positioned so as to be acted upon by a rotor of the peristaltic pump, for example, in a raceway or semi-circular track.

The pressure sensor can be operatively connected to the gas side of the pressure pod and can be configured for sensing pressure resulting from movement of the diaphragm. To maintain the diaphragm in a mid-section or mid-body position in the interior of the pressure pod, for example, to accurately sense increases and decreases in the pressure of fluid flowing through the pressure pod, it may become necessary to vent gas from the gas side of the pressure pod, or to pressurize the gas side of the pressure pod, or to do both. A gas source can be provided in fluid communication with the gas side of the pressure pod and can comprise a valve and/or regulator configured to provide a fluid communication between the gas side and the gas source. The valve and/or regulator can also be configured to interrupt communication between the gas side and the gas source, for example, to prevent the gas source from pressurizing or further pressurizing the gas side. The valve and/or regulator can be configured to take on an open or venting position to thereby form a fluid communication between the gas side and a vent port, for example, a vent port leading to an ambient atmosphere. In the open or venting position, the valve and/or regulator can enable pressurized gas to escape from the gas side of the pressure pod, for example, to release pressure from the gas side, which pressure may have caused the diaphragm to have moved too far towards the flow-through fluid side and away from a more mid-body position. As mentioned before, the mid-body position is often a preferred diaphragm position for sensing pressure fluctuations. Herein, while many references are made to a valve or to valves, it is to be understood that a regulator is considered herein to constitute one type of valve that can be used.

In one or more embodiments of the present teachings, the fluid pump can comprise a peristaltic pump and the pressure sensor can be configured for sensing pulses of pressure caused by the peristaltic pump moving fluid through flow-through fluid side of the pressure pod. The controller can be configured to compare a pressure signal received from the pressure sensor, to a predetermined pressure signal, for example, to a predetermined pressure signal that corresponds to a signal generated during normal operation of the pressure pod, under normal operating pressures, and where the diaphragm is properly or optimally positioned. In some cases, the controller can be configured to determine whether the pressure signal received is within an acceptable degree of variance relative to the predetermined pressure signal. A standard deviation can be calculated based on the difference between the pressure signal received from the pressure sensor and the predetermined pressure signal. The standard deviation can be compared to threshold values, for example, compared to maximum and minimum threshold values, to determine whether the pressure pod is working properly and/or whether the diaphragm is properly positioned within the pressure pod.

The pressure signal received from the pressure sensor can be compared to a plurality of predetermined signals. At least one of the plurality of predetermined signals can correspond to a signal generated by operation of the pressure pod when the diaphragm is in a first extreme position. The first extreme position can be, for example, a position where the gas side of the pressure pod is minimized, and the flow-through fluid side of the pressure pod is maximized. Such a position of the diaphragm would be undesirable and would prevent the pressure pod from generating increased pressure pulses because the diaphragm would already be in a fully extended or fully pressurized position. In such a position, the diaphragm would not be able to move further in response to increased gas pressure and thus would not be capable of delivering a pressure pulse to the pressure sensor. The pressure signal received from the pressure sensor can be compared to a predetermined signal generated when the diaphragm was in a second extreme position wherein the flow-through fluid side of the pressure pod is minimized, and the gas side of the pressure pod is maximized. In the second extreme position, the diaphragm would have been fully extended toward the flow-through fluid side such that any further decreases in pressure would not be able to be detected.

If the controller determines that the pressure signal received from the pressure sensor is similar to the predetermined signals whereby the diaphragm had been in one of the extreme positions, then the controller can actuate the gas source and valve to pressurize or vent the gas side of the pressure pod. In so doing, the diaphragm can be moved to a more mid-body position within the pressure pod. Logic circuitry known to those skilled in the art can be provided to enable the controller to control the valve, gas source, or both, to either vent the gas from the gas side, pressurize the gas side with the gas source, or both, as appropriate. In so doing, the position of the diaphragm can be adjusted. If the pressure signal received from the pressure sensor is determined to be similar to a predetermined pressure signal corresponding to normal operation of the pressure pod, then the controller can maintain the valve, and gas source, in the then-current states such that no adjustments are made or deemed necessary.

The pressure signal can be periodically, intermittently, randomly, or continuously sent to and received by the controller. Upon making an adjustment to the gas pressure in the gas side, the controller can pause or wait before comparing the resulting pressure to the predetermined signals. In some cases, the controller can immediately compare the new pressure signal resulting from an adjustment, to one or more predetermined signals.

The pressure signal generated by the pressure sensor can be more than one second in length, for example, along a time axis. The signal can be generated over a period of time, for example, over a period of two seconds, three seconds, five seconds, seven seconds, ten seconds, or longer. The length of the pressure signal can be equal to the amount of time it takes for the pump to produce one, two, three, or more pulses of pressure. In some cases, a peristaltic pump is used and the signal to be compared is generated over the amount of time needed for the pump to generate two, three, or four pressure pulses.

The gas source can comprise pressurized gas under a pressure of greater than 1 atmosphere, for example, under a pressure of 1.5 atmospheres, under a pressure of 2 atmospheres, under a pressure of 3 atmospheres, or more. The gas source can comprise gas under pressure of from 1.1 atmospheres to 100 atmospheres, of from 1.1 atmospheres to 10 atmospheres, of from 1.1 atmospheres to 5 atmospheres, or of from 1.5 atmospheres to 3.0 atmospheres. In some cases, the gas source can comprise a gas compressor and a tank for holding pressurized gas, for example, at a pressure of from about 5 psig to about 150 psig, of from about 10 psig to about 100 psig, or of from about 15 psig to about 50 psig. The gas source can comprise pressurized air, carbon dioxide, nitrogen, another inert gas, or the like. The gas source can comprise a gas pump or an inflator.

The valve can be configured to be a part of the gas source, or simply in fluid communication with the gas source. In some cases, the valve can comprise two valves, one for controlling a fluid communication between the gas side and the gas source, and one used for controlling a vent to vent gas pressure from the gas side of the pressure pod. In some cases, the valve, or each valve, can comprise a T-valve, a pin valve, a threaded closure valve, a numerically-operated valve, a hydraulically-operated valve, or the like. The valve can comprise a multi-wave valve, for example, a valve that can assume a closed state, a venting state whereby gas pressure in the gas side of the pressure pod can be vented, and a gas inlet state whereby pressurized gas from the gas source can be in fluid communication with the gas side of the pressure pod. Operation of the valve, or of each valve, can be controlled by the controller, by using, for example, control logic, servo-motors, stepper motors, pneumatics, hydraulics, combinations thereof, and the like.

Any one of a variety of valves can be used as part of, or in connection with the gas source. The valve can be selected from any of the following types: a ball valve; a butterfly valve; a check valve; a gate valve; a needle valve; a quarter-turn valve; a flow control valve; a gas pressure regulator; a plunger valve; a pressure regulator; a pressure reducing valve; a pressure sustaining valve; a back-pressure regulator; a saddle valve; a safety valve; a relief valve; a solenoid valve; and a stopcock. The valve can be controlled by any of a variety of systems and devices. The valve or valves can be controlled by actuators, for example, attached to a valve stem. The actuators can be electromechanical actuators, including, for example, an electric motor or solenoid, pneumatic actuators that are controlled by air pressure, or hydraulic actuators that are controlled by the pressure of a liquid such as oil or water. Actuators can be used for automatic control, remote control, or a combination thereof. Pneumatic actuators and hydraulic actuators can be used that work based on pressurized air or liquid lines. A pilot valve can be used to control one or more other valves. Pilot valves in actuator lines can be used to control the supply of air or liquid going to actuators. In some valve designs, the pressure of the gas flow itself or a pressure difference of the gas flow between ports can be used to automatically control flow through the valve.

The pressure sensor can be a modular unit, a permanent unit, a replaceable unit, or the like. The pressure sensor, being in fluid communication with the gas side of the pressure pod, does not come into contact with the fluid flowing through pressure pod on the flow-through fluid side. Therefore, at no time is the pressure sensor contaminated by the fluid and thus the pressure sensor can be configured as a re-usable component of the system.

The pressure sensor can comprise an inlet port into which a pressure line, such as pressure tubing or air tubing, can be connected to form a fluid communication between the gas side of the pressure pod and the pressure sensor. The gas side of the pressure pod can have a port. The gas side port and the inlet port for the pressure sensor can have the same inner diameter, the same outer diameter, or both, for example, so that a pressure tube of fixed outer diameter can be connected to both the gas side of the pressure pod and to the inlet port of the pressure sensor.

The pressure sensor can comprise one or more of the pressure sensors described, for example, in any of U.S. Pat. No. 8,210,049 B2, U.S. Pat. No. 8,092,414 B2, U.S. Pat. No. 6,526,357 B1, U.S. Pat. No. 3,863,504, and European Patent Application Publication No. 0 30 891 A1, each of which is incorporated herein in its entirety, by reference.

Figure 1B:
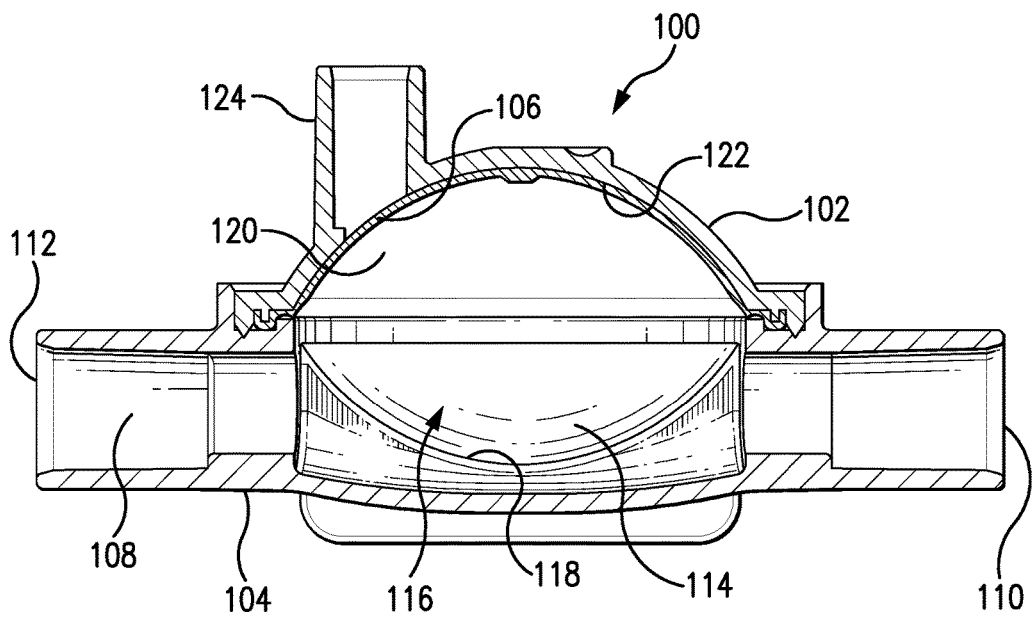
FIG. 1B is a cross-sectional side view of the pressure pod shown in FIG. 1A, but wherein the diaphragm is shown and is positioned in an extreme upper position against the upper inner sidewall of the pressure pod.

With the reference to the drawing figures, FIG. 1A is a perspective view in partial cross-section showing a flow-through pressure pod, with the diaphragm removed, that can be used in accordance with the present teachings. FIG. 1B shows a cross-sectional side view of the pressure pod shown in FIG. 1A, but wherein the diaphragm is shown and is positioned in an extreme upper position against the upper inner sidewall of the pressure pod. As can be seen in FIGS. 1A and 1B, pressure pod 100 comprises an upper shell 102, a lower shell 104, and a diaphragm 106. Lower shell 104 can be configured, as shown, to define a flow-through tube 108 that includes an inlet port 110 and an outlet port 112. Lower shell 104 also defines a bottom half 114 of a diaphragm chamber 116. Bottom half 114 of diaphragm chamber 116 includes an inner sidewall 118. Upper shell 102 defines an upper half 120 of diaphragm chamber 116 and includes an inner sidewall 122. As can be seen in FIG. 1B, diaphragm 106 is pressed up against inner sidewall 122 of diaphragm chamber 116 in an extreme upper position. If the pressure of fluid traveling through flow-through tube 108 increases, diaphragm 106 would not be able to move any further upwardly and the pressure pod would not be able to generate a detectable corresponding gas pressure increase to signify the increase in fluid pressure.

Upper shell 102 defines a pressure port 124 through which gas on the upper side of diaphragm 106 can travel, for example, upwardly through pressure port 124 and into a pressure line (not shown) that can be in operable fluid communication with a pressure sensor (not shown). As diaphragm 106 moves downwardly, gas can be pulled into upper half 120 of diaphragm chamber 116 through pressure port 124 resulting in a pressure decrease that can be detected by the pressure sensor. Changes in gas pressure of gas in pressure port 124, in the pressure line, and on the upper side of diaphragm 106, can be sensed by the pressure sensor and used to determine a pressure of fluid flowing through flow-through tube 108.

Figure 2:
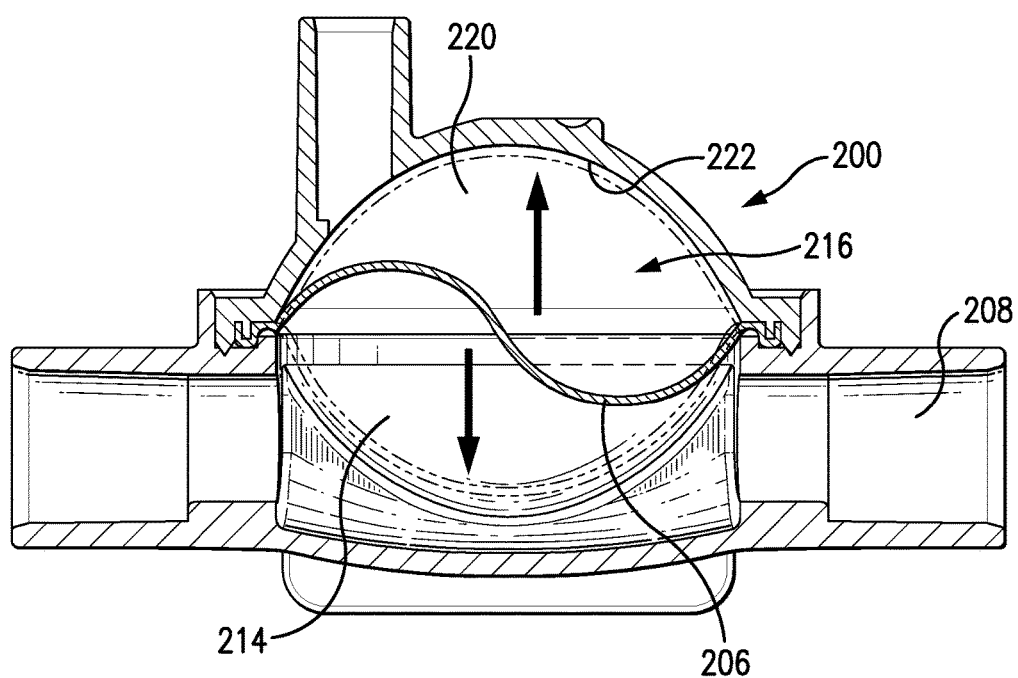
FIG. 2 is a schematic, cross-sectional view of a pressure pod including a diaphragm shown in a mid-body position between a lower half and an upper half of a diaphragm chamber.

FIG. 2 is a schematic, cross-sectional view of a pressure pod 200 that is similar to pressure pod 100 shown in FIGS. 1A and 1B. In FIG. 2, a diaphragm 206 is shown in a mid-body position between a lower half 214 and an upper half 220 of a diaphragm chamber 216. The upward pointing arrow denotes the direction of travel that diaphragm 206 can undergo when exposed to increases in pressure of fluid flowing through flow-through tube 208. The dashed line shown along an upper inner sidewall 222 of diaphragm chamber 216 denotes an extreme upper position that diaphragm 206 can take under maximum detectable pressure conditions. The downward pointing arrow denotes the direction diaphragm 206 can move when diaphragm 206 is exposed to negative or low-pressure conditions due to decreases in the pressure of fluid flowing through flow-though tube 208. The dashed line at the bottom of diaphragm chamber 216 denotes an extreme lower position that diaphragm 216 can take under minimum detectable pressure conditions.

Figure 3:
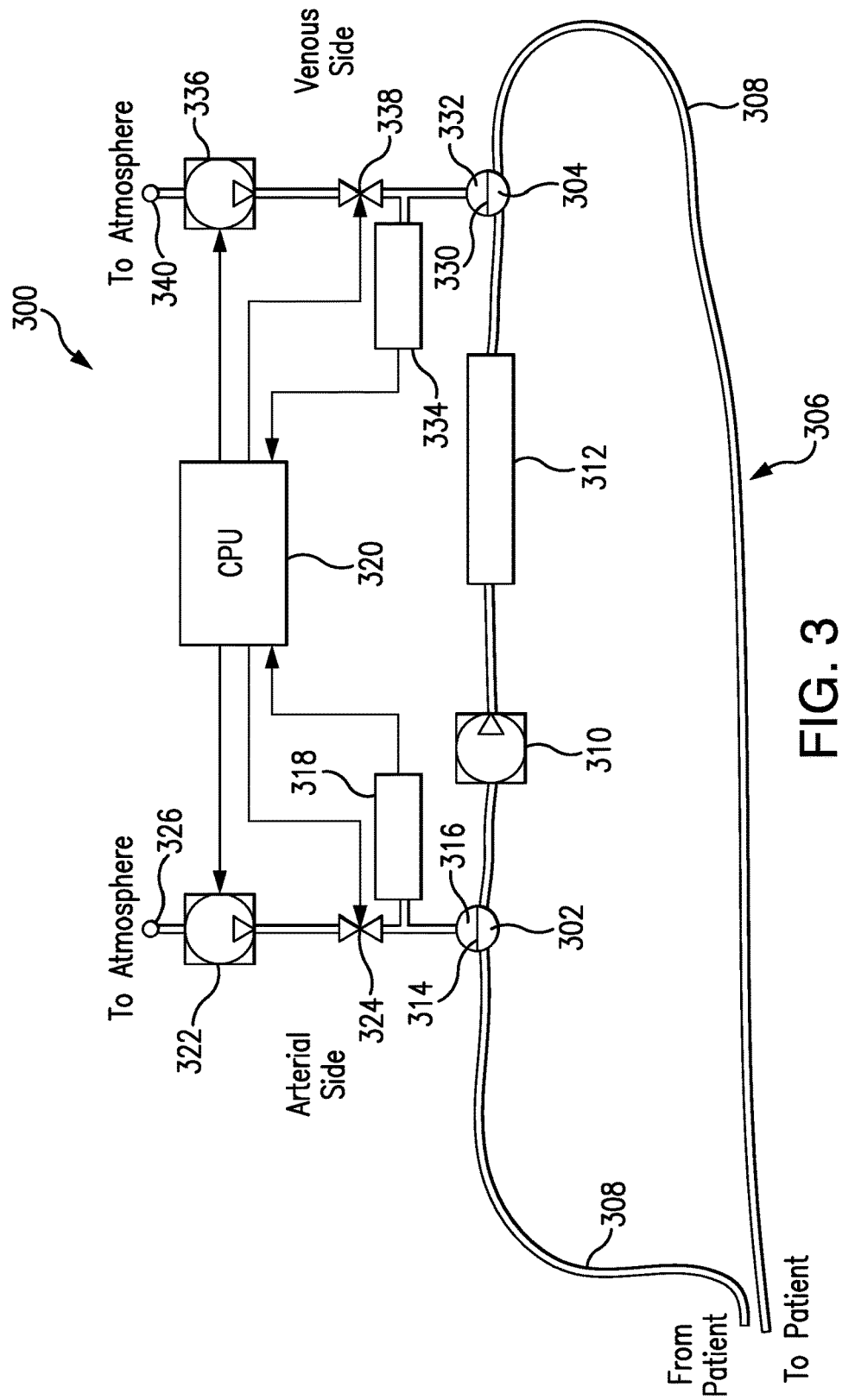
FIG. 3 is a schematic illustration of a pressure pod diaphragm control system in the form a block diagram, showing a system in accordance with the present teachings and comprising both an arterial side pressure pod and a venous side pressure pod.

FIG. 3 is a schematic illustration of a pressure pod diaphragm control, block diagram showing an exemplary system 300 comprising both an arterial side pressure pod 302 and a venous side pressure pod 304, and showing system components for controlling both. As shown in FIG. 3, a blood circuit 306 includes a bloodline 308 that forms a fluid communication from a patient to an arterial side pressure pod 302 and from pressure pod 302 to a blood pump 310. Bloodline 308 then includes a fluid communication from blood pump 310 to a dialyzer 312, and from dialyzer 312 to venous side pressure pod 304. Bloodline 308 then returns blood to a patient after it flows through pressure pod 304. Arterial side pressure pod 302 includes a diaphragm 314. Diaphragm 314 divides pressure pod 302 into a flow-through fluid half below diaphragm 314, and a gas half 316 that is in fluid communication with a pressure sensor 318. Pressure sensor 318 senses gas pressure within gas half 316 of pressure pod 302 and sends a signal representative of the gas pressure to a central processing unit (CPU) 320. Based on the signal received from pressure sensor 318, CPU 320 can determine whether or not adjustments are needed to the position of diaphragm 314. For example, when the pressure signal indicates that pressure within the gas half 316 is within an acceptable range and pressure increases and decreases are being properly detected, CPU 320 can determine that no adjustments are needed to the position of diaphragm 314. If, on the other hand, based on the signal sent from pressure sensor 318, CPU 320 determines that more gas pressure is needed in gas half 316, CPU 320 sends a signal to activate an air pump 322 that can force pressurized gas into gas half 316 through a valve 324. Valve 324 can comprise, for example, a two-way valve as shown. Simultaneously, CPU 320 can send a signal to valve 324 so that valve 324 is opened and pressurized gas generated by air pump 322 can be forced into gas half 316. By controlling air pump 322 and valve 324 based on signals received from pressure sensor 318, CPU 320 can regulate the gas pressure in gas half 316 and thus maintain diaphragm 314 in a mid-body position within pressure pod 302. The mid-body position enables diaphragm 314 to move upwardly or downwardly as a result of pressure increases and decreases, respectively, in the segment of bloodline 308 coming from the patient.

On the venous side of system 300, blood that has been pumped by blood pump 310 along bloodline 308, and through dialyzer 312, passes through venous side pressure pod 304. Pressure increases and decreases, including pressure pulses, of blood passing through pressure pod 304, are detected by movement of a diaphragm 330 within pressure pod 304. Similar to the construction of pressure pod 302, pressure pod 304 includes a gas half 332 defined as the volume above diaphragm 330. Pressure changes in the gas in gas half 332 are detected by a pressure sensor 334 that sends a signal to CPU 320. CPU 320 receives the pressure signal from pressure sensor 334 and controls an air pump 336 and a valve 338 to regulate the pressure within gas half 332. If the gas pressure within gas half 332 exceeds a maximum, threshold, and/or predetermined value, CPU 320 can control valve 338 and air pump 336 such that gas from gas half 332 can be vented through valve 338, through air pump 336, and out through a vent 340. Then, diaphragm 330 can assume a more mid-body position within the diaphragm chamber of pressure pod 304. If the gas pressure with gas half 332 falls below a minimum, threshold, and/or predetermined value, CPU 320 can control valve 338 and air pump 336 such that gas can be pumped by air pump 336 though valve 338 and into gas half 332 so that diaphragm 330 can assume a more mid-body position within the diaphragm chamber of pressure pod 304.

Figure 4:
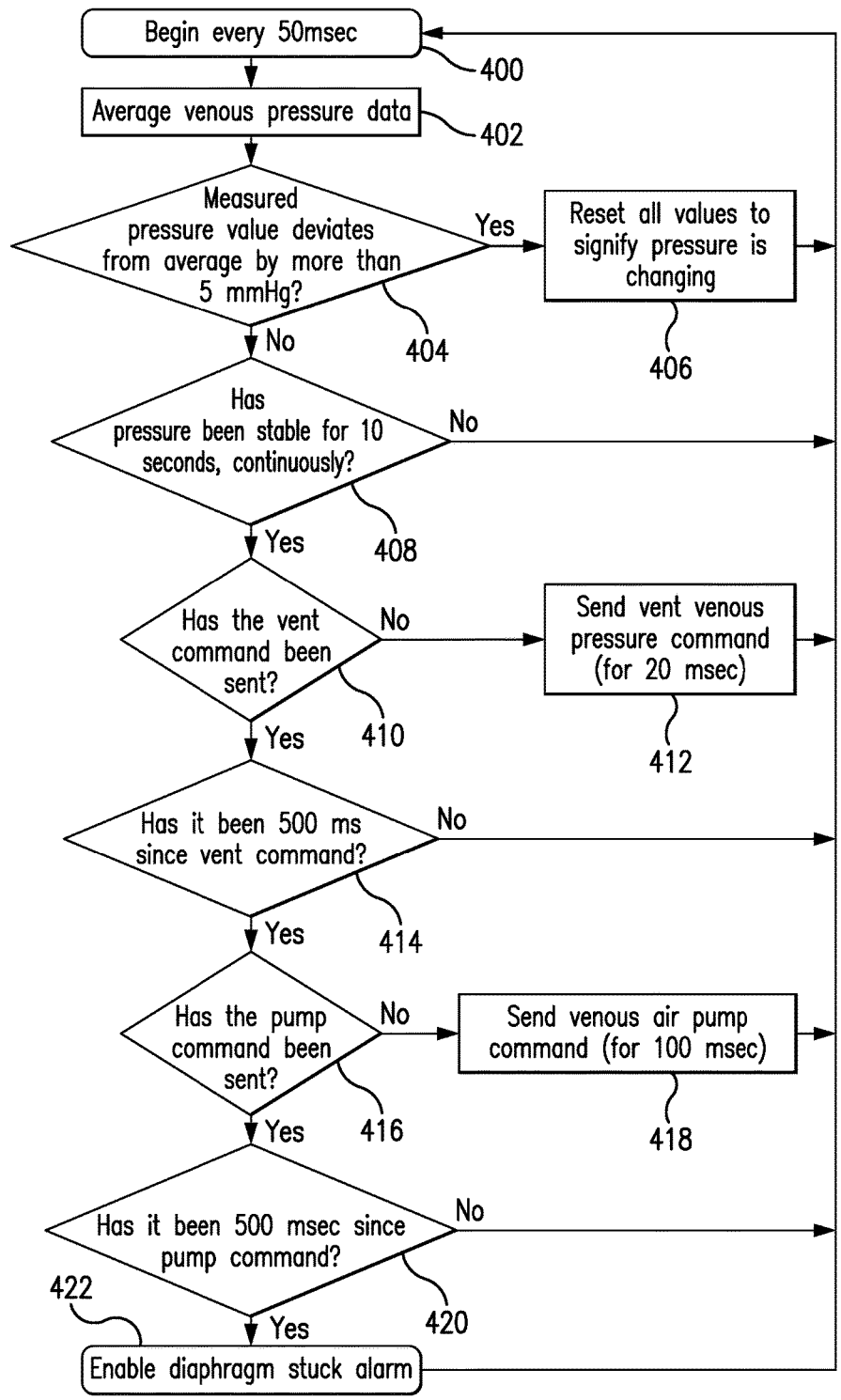
FIG. 4 is a process flow diagram showing the algorithm involved with automatically controlling the position of a pressure pod diaphragm, in accordance with various embodiments of the present teachings.

FIG. 4 is a process flow diagram showing the algorithm involved with automatically controlling the position of a pressure pod diaphragm, in accordance with the present teachings. The algorithm can be used for controlling each pressure pod of the system, for example, in a system comprising in arterial side pressure pod and a venous side pressure pod, each pressure pod can be controlled independently of the other. For the algorithm shown in FIG. 4, control of a venous side pressure pod is exemplified. As shown in FIG. 4, once a dialysis treatment commences, gas pressure on the gas side of the venous pressure pod is detected by a pressure sensor. A signal corresponding to the sensed pressure is sent to a CPU. As shown in step 400, pressure on the gas side of the venous pressure pod can be sensed by the pressure sensor and a corresponding signal can be sent to the CPU every 50 milliseconds (msec). The CPU can then average the pressure signals received every 50 msec to generate average venous pressure data in a step 402. Each new incoming pressure signal received by the CPU is then compared to the average venous pressure data (the average value) and a determination is made in step 404 as to whether the measured value deviates from the average value by more than 5 mmHg. If the measured pressure does deviate from the average by than 5 mmHg, then the CPU, in a step 406, can reset all the values and indicate that the pressure in the gas half of the venous pressure pod is changing. In response, a new set of pressure readings can be taken over a fresh interval of time and a new average venous pressure data value can be generated. If, on the other hand, the pressure measured deviates from the average value by not more than 5 mmHg, then the CPU determines that the pressure is stable and, in a step 408, the CPU determines whether the pressure remains stable for 10 seconds, continuously. If the pressure does not remain stable for 10 seconds continuously, such that a new measured pressured value does deviate from the average value by more than 5 mmHg, then the CPU makes a determination that the venous side pressure pod diaphragm is correctly positioned and no adjustments to the gas pressure in the gas half of the pressure pod are made. On the other hand, if the CPU determines that the pressure has remained stable for 10 seconds continuously, then the CPU determines, in a step 410, whether a vent command has been sent. If the CPU determines that a vent command has not been sent, then, in a step 412, the CPU sends a vent venous pressure command, for example, to activate a venting function for 20 msec, and steps 400, 402, and 404 are repeated. A new pressure value is then sensed, and operation is continued. If the venting does not correct the positioning of the diaphragm and instead the pressure continues to remain stable, then, in step 410, the CPU determines whether 500 msec have elapsed since the vent command has been sent. If, in step 414, the CPU determines that 500 msec have not elapsed, then the system continues to monitor the pressure at 50 msec intervals. If, in step 414, the CPU determines that 500 msec have elapsed since the vent command has been sent, then the CPA determines, in a step 416, whether a pump command has been sent. If a pump command has not been sent, then in a step 418, the CPU sends a venous air pump command, for example, for 100 msec, and steps 400, 402, and 404 are repeated. If, in step 416, the CPU determines a pump command has been sent, then the CPU determines, in a step 420, whether 500 msec have elapsed since the pump command was sent. If, in step 420, it is determined that it has not been 500 msec since the pump command has been sent, then steps 400, 402, and 404 are repeated and the system continues to monitor the pressure at 50 msec intervals. If 500 msec have elapsed since the pump command has been sent, as determined in step 420, and the pressure continues to remain stable, then the CPU determines the diaphragm is stuck and the CPA enables a stuck alarm. The alarm can be an audible alarm, a flashing light, a combination thereof, or the like.

Figure 5A:
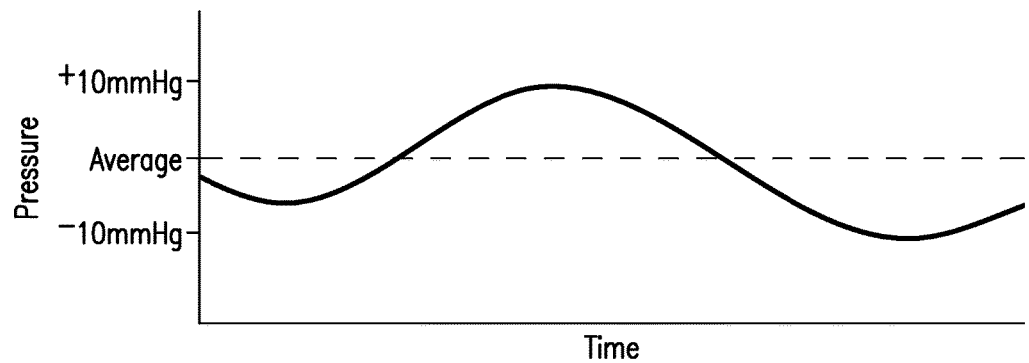
FIGS. 5A-5C are three graphs showing waveforms representing pressure signals generated by an arterial side pressure pod, over time, including a graph that corresponds to pressure measurements taken under normal, proper operating conditions (FIG. 5A), a graph that corresponds to pressure measurements taken under conditions wherein the pressure pod diaphragm is stuck in a first, extreme, over-pressurized position (FIG. 5B), and a graph that corresponds to pressure measurements taken under conditions wherein the pressure pod diaphragm is stuck in a second, extreme, under-pressurized position (FIG. 5C).
Figure 5B:
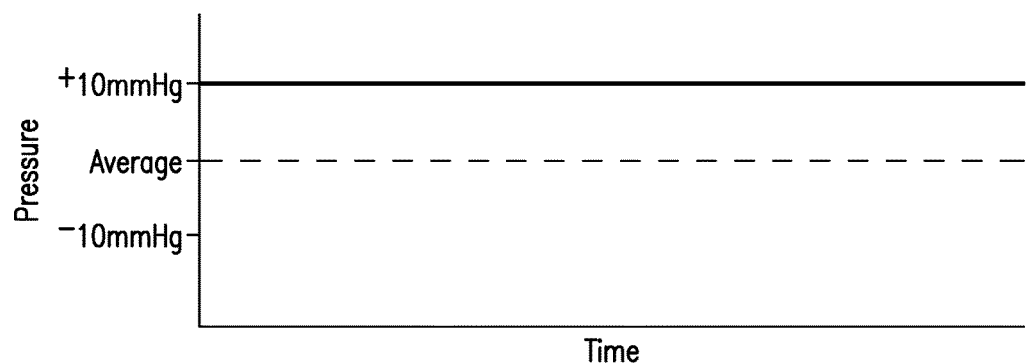
Figure 5C:
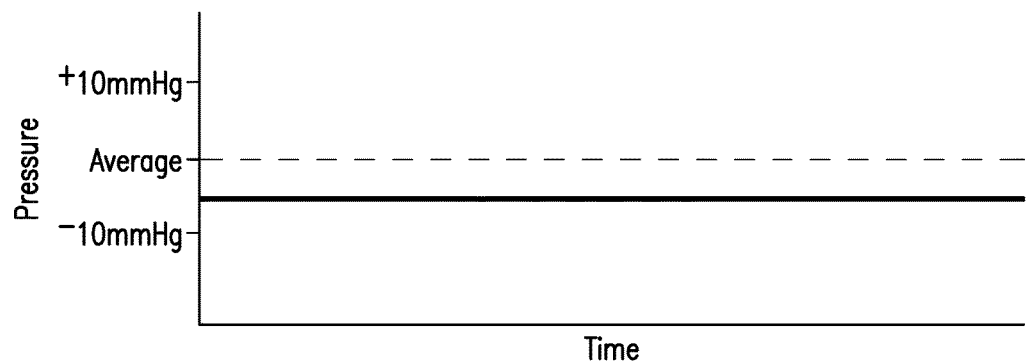

In addition, or as an alternative, the CPU can receive pressure signals as, or translate pressure signals to, a waveform, and the waveform can be analyzed by the CPU to determine whether pressure fluctuations are properly being detected and to determine whether adjustments need to be made to the gas pressure in the gas half of the pressure pod so as to adjust the position of the diaphragm. FIGS. 5A-5C show exemplary waveforms with which the CPU can compare incoming pressure signals shaped as waveforms. More particularly, FIGS. 5A-5C are three graphs showing waveforms representing pressure signals generated by an arterial side pressure pod, over time, including a graph that corresponds to pressure measurements taken under normal, proper operating conditions (FIG. 5A), a graph that corresponds to pressure measurements taken under conditions wherein the pressure pod diaphragm is stuck in a first, extreme, over-pressurized position (FIG. 5B), and a graph that corresponds to pressure measurements taken under conditions wherein the pressure pod diaphragm is stuck in a second, extreme, under-pressurized position (FIG. 5C). By comparing a waveform generated in real-time to various stored waveforms, such as those shown in FIGS. 5A-5C, the CPU can determine whether the waveform generated in real-time, shows sufficient fluctuations in pressure, over time, to conclude that the pressure pod diaphragm is properly positioned. By making such a comparison, the CPU can also determine whether the waveform is so substantially linear and non-fluctuating that the pressure pod diaphragm must be stuck and not properly positioned, in which case corrective action can be taken or an alarm can be activated.

The entire contents of all references cited in this disclosure are incorporated herein in their entireties, by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether such a range is separately disclosed. Where a range of numerical values is recited herein, unless otherwise stated, the range is intended to include the endpoints thereof, and all integers and fractions within the range. It is not intended that the scope of the invention be limited to the specific values recited when defining a range.

All patents, patent applications, and publications mentioned herein are incorporated herein in their entireties, by reference, unless indicated otherwise.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A system for controlling the position of a diaphragm in a diaphragm-containing pressure pod, the system comprising;
    a fluid pump:
    a pressure pod comprising an interior defining a flow-through fluid side and a gas side, the flow-through fluid side and the gas side being separated from one another by a diaphragm;
    a fluid conduit in fluid communication with the flow-through fluid side and operatively positioned with respect to the fluid pump such that the pump can move fluid through the conduit and force fluid through the flow-through fluid side of the pressure pod;
    a pressure sensor operatively connected to the gas side of the pressure pod and configured for sensing pressure resulting from movement of the diaphragm;
    a gas source in fluid communication with the gas side of the pressure pod and comprising a valve configured to provide fluid communication between the gas side and the gas source, the valve also being configured to interrupt communication between the gas side and the gas source; and
    a controller configured to (1) receive a pressure signal generated by the pressure sensor, (2) compare the pressure signal received to a predetermined pressure signal that corresponds to a signal generated during normal operation of the pressure pod, under normal operating pressures and where the diaphragm is properly or optimally positioned, (3) calculate a difference between the pressure signal received from the pressure sensor and the predetermined pressure signal, and (4) control the valve in response to the calculated difference, wherein the control of the valve controls pressure in the gas side of the pressure pod, which in-turn controls the position of the diaphragm.

2. The system of claim 1, wherein the controller is further configured such that, after controlling the valve and in-turn controlling the position of the diaphragm to make an adjustment, the controller immediately compares a new pressure signal resulting from the adjustment, to one or more predetermined signals.

3. The system of claim 1, wherein the controller comprises an oscilloscope, is configured to display pressure signals it receives from the pressure sensor as a waveform on the oscilloscope, and is configured to compare the waveform to one or more predetermined waveforms.

4. The system of claim 3, wherein the controller comprises a memory, the one or more predetermined waveforms are stored in the memory, and the one or more predetermined waveforms include a first waveform corresponding to a signal received when the diaphragm is in a first extreme position, and a second waveform corresponding to a signal received when the diaphragm is in a second extreme position opposite the first extreme position.

5. The system of claim 4, wherein the first extreme position of the diaphragm is a position wherein the flow-through fluid side of the pressure pod has a maximum volume and the gas side of the pressure pod has a minimum volume, and the second extreme position of the diaphragm is a position wherein the volume of the flow-through fluid side of the pressure pod is minimized and the volume of the gas side of the pressure pod is maximized.

6. The system of claim 1, wherein the controller is configured to compare a pressure signal received from the pressure sensor to a predetermined pressure signal corresponding to normal operation of the pressure pod, and the controller is configured to determine whether the pressure signal received is within an acceptable degree of variance relative to the predetermined pressure signal.

7. The system of claim 1, wherein the fluid pump comprises a peristaltic pump and the pressure sensor is configured for sensing pulses of pressure caused by the peristaltic pump moving fluid through the flow-through fluid side.

8. The system of claim 1, wherein the valve is configured to move between an open position and a closed position, and the valve is configured in the open position to provide a gaseous communication between the gas side and an ambient atmosphere while fluid is being moved through the flow-through fluid side.

9. The system of claim 1, further comprising a fluid within the conduit, wherein the fluid comprises blood and the gas source comprises pressurized gas under a pressure of greater than 1 atmosphere.

10. A method for automatically adjusting the position of a diaphragm in a pressure pod, the method comprising;
    forcing a fluid a through a flow-through fluid side of a pressure pod, using a pump, the pressure pod comprising a diaphragm, the flow-through fluid side being disposed on one side of the diaphragm, and a gas side being disposed on a side of the diaphragm opposite the flow-through fluid side;
    generating a pressure signal corresponding to the pressure of fluid flowing through the flow-through fluid side of the pressure pod, over time;
    comparing the pressure signal to one or predetermined pressure signals that correspond to a signal generated during normal operation of the pressure pod, under normal operating pressures and where the diaphragm is properly or optimally positioned; and
    (i) releasing pressure from the gas side of the pressure pod, (ii) pressurizing the gas side of the pressure pod, or both (i) and (ii), based on the comparison,
    wherein the releasing pressure, the pressurizing, or both, are used to properly position the diaphragm between the flow-through fluid side and the gas side of the pressure pod.

11. The method of claim 10, wherein the comparing comprises comparing the pressure signal to a plurality of predetermined pressure signals.

12. The method of claim 10, wherein the releasing pressure, pressurizing, or both, comprises actuating a valve that is in fluid communication with the gas side of the pressure pod, to maintain the diaphragm in a mid-body position in the pressure pod.

13. The method of claim 10, wherein the releasing pressure, pressurizing, or both, comprises pressurizing the gas side of the pressure pod, and the pressurizing comprises opening a valve to form a fluid communication between the gas side of the pressure pod and a pressurized gas source so that pressurized gas from the pressurized gas source enters the gas side of the pressure pod, to maintain the diaphragm in a mid-body position in the pressure pod.

14. The method of claim 10, wherein the releasing pressure, pressurizing, or both, comprises releasing pressure from the gas side of the pressure pod, and the releasing pressure comprises opening a valve to form a fluid communication between the gas side of the pressure pod and an ambient atmosphere, the opening causing pressurized gas in the gas side of the pressure pod to vent gas from the gas side to the ambient atmosphere, to maintain the diaphragm in a mid-body position in the pressure pod.

15. The method of claim 10, wherein the pump comprises a peristaltic pump and the pressure signal comprises pressure pulses resulting from the peristaltic pump moving the fluid through the flow-through fluid side of the pressure pod.

16. The method of claim 10, wherein the comparing comprises comparing the pressure signal to one or more predetermined pressure signals.

17. The method of claim 10, wherein the comparing comprises comparing the pressure signal to one or more predetermined waveforms.

18. The method of claim 10, wherein the comparing comprises calculating an average deviation of the generated pressure signal relative to a predetermined signal, and determining whether the calculated average deviation is within an acceptable range of deviation.

19. The method of claim 10, wherein the releasing, pressurizing, or both, comprises:
    venting gas from the gas side of the pressure pod;
    generating a new pressure signal, after the venting, corresponding to the pressure of fluid flowing through the flow-through fluid side of the pressure pod;
    determining that the new pressure signal does not substantially deviate from an average pressure signal;
    pressurizing the gas side of the pressure pod after generating the new pressure signal; and
    generating yet another pressure signal, all while fluid is being moved through the flow-through fluid side.

20. The method of claim 19, wherein the determining that the new pressure signal does not substantially deviate from the average pressure signal comprises determining whether the new pressure signal corresponds to a pressure that is at least 5 mmHg higher or lower than the average pressure signal.

21. The method of claim 10, wherein the releasing, pressurizing, or both, results in an adjustment of the position of the diaphragm and a new pressure signal, and the method further comprises, after the releasing, pressurizing, or both, immediately comparing the new pressure signal to one or more predetermined signals.

* * * * *